| United States Patent [19] | [11] | 4,440,951 |
|---|---|---|
| Drake | [45] | Apr. 3, 1984 |

[54] PROCESS FOR PREPARATION OF AMINOBENZALDEHYDES AND AMINOBENZYLKETONES

[75] Inventor: Charles A. Drake, Bartlesville, Okla.

[73] Assignee: Phillips Petroleum Company, Bartlesville, Okla.

[21] Appl. No.: 441,585

[22] Filed: Nov. 15, 1982

[51] Int. Cl.³ ............................................. C07C 85/18
[52] U.S. Cl. ..................................................... 564/305
[58] Field of Search ......................................... 564/305

[56] References Cited

U.S. PATENT DOCUMENTS

| 3,316,261 | 4/1967 | Speranza et al. | 564/305 X |
| 4,273,785 | 6/1981 | Shepherd | 564/305 X |

FOREIGN PATENT DOCUMENTS 57927 8/1969 Poland ................................ 564/305

OTHER PUBLICATIONS

J. Chem. Soc., 1945, pp. 276–277, (1945).
Chem. Abs., 62, p. 7691g, (1965).

*Primary Examiner*—Paul F. Shaver

[57] ABSTRACT

An improved process for the formation of a dihydrocarbylaminobenzaldehyde or a dihydrocarbylaminobenzylketone is provided consisting of reacting a dihydrocarbylaniline and a protected Schiff's base in the presence of water, a carboxylic acid, and an aromatic hydrocarbon.

7 Claims, No Drawings

PROCESS FOR PREPARATION OF AMINOBENZALDEHYDES AND AMINOBENZYLKETONES

This invention relates to an improved process for the synthesis of aminobenzaldehydes and aminobenzylketones.

It is known to one skilled in the art that N,N-dialkylaminobenzaldehyde can be prepared by reacting N,N-dialkylaniline and a hexalkylenetetramine in the presence of a carboxylic acid and water and then hydrolyzing the resulting reaction product. For example, Polish Pat. No. 57,927 discloses a two-step reaction for the production of p-dimethylaminobenzaldehyde by reaction of N,N-dimethylaniline with hexamethylenetetramine in the presence of water and acetic acid followed by hydrolysis of the Schiff's base reaction product. In some instances, though, elimination of the hydrolysis step is desirable because a one-step reaction will allow for easier product isolation.

Since aminobenzaldehydes and aminobenzylketones are useful for production of viscosity index improvers and N-containing polymers for blending with other polymers to improve impact resistance, a process which would simplify and improve their production is desirable.

Therefore, it is an object of this invention to provide an improved process for the production of aminobenzaldehydes and aminobenzylketones.

Other aspects, objects, and advantages of the present invention will become apparent from the specification and the claims.

In accordance with the present invention I have discovered that aminobenzaldehydes and aminobenzylketones may be synthesized in one step by the addition of an aromatic hydrocarbon to the reaction. In particular I have discovered that a one-step reaction is achieved by a process consisting of reacting N,N-dialkylaniline and a protected Schiff's base, in the presence of a carboxylic acid, an aromatic hydrocarbon, and water. The need for a subsequent hydrolysis step, with additional handling and chemical requirements is thereby eliminated. The desired reaction product is isolated directly from the reaction mixture by phase separation and solvent removal, the solvent thus recovered being suitable for recycle.

The aminobenzaldehydes and aminobenzylketones produced by the process of the present invention are defined by the formula

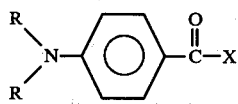

wherein R is a $C_1$ to $C_8$ hydrocarbyl radical and X is either hydrogen or a $C_1$ to $C_{10}$ hydrocarbyl radical. Examples of these aminobenzaldehydes include p-dimethylaminobenzaldehyde, p-diethylaminobenzaldehyde, and p-dihexylaminobenzaldehyde. Examples of these benzylketones include p-dimethylaminobenzyl methyl ketones and p-dimethylaminobenzyl ethyl ketones. N,N-hydrocarbyl anilines suitable for use in this invention may be represented by the formula:

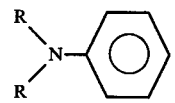

wherein R is as previously defined. Examples include N,N-dimethylaniline, N,N-diethylaniline, and N,N-dihexylaniline.

Protected Schiff's bases used in the present invention are stable products derived from the reaction of ammonia with a $C_1$ to $C_{11}$ aldehyde. In general the reaction product of R'CHO with ammonia, where R' is the same as X defined above is suitable. Most conveniently employed is hexamethylenetetramine, obtained by reaction of formaldehyde with ammonia.

Carboxylic acids useful in the present invention are defined by the formula R"COOH wherein R" is either H or a $C_1$ to $C_6$ alkyl radical. Examples of these carboxylic acids include formic acid, acetic acid, propionic acid, butyric acid and caproic acid.

Aromatic hydrocarbons suitable for use in the present invention are represented by the formula:

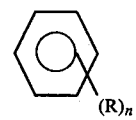

wherein R is the same as previously defined and n can be any whole number from 0–6. Examples of such compounds include toluene, m-xylene, p-xylene, isopropyl benzene and mixtures thereof.

The process of the present invention employs the reagents in the following amounts based upon 1 mole of the N,N-hydrocarbyl aniline:

| Ingredient | Mole Ratio of Ingredient | |
|---|---|---|
| | Broad | Preferred |
| Protected Schiff's base | .1–10 | .2–2 |
| Carboxylic Acid | .5–20 | 1–10 |
| $H_2O$ | 1–20 | 2–10 |
| Aromatic Compound | 1–20 | 2–10 |

The present invention can be carried out at a temperature broadly from about 100° C. to about 250° C., preferably from about 120° C. to about 175° C. Reaction time can vary broadly from about 15 minutes to about 12 hours, preferably from one-half to about 4 hours. Although reaction pressure has not been found to be critical, the reaction can be carried out from atmospheric up to about 2000 psig. Preferably the reaction will be carried out at autogeneous pressure, or from about 100 to about 500 psig.

The present invention can also be carried out in a continuous as well as batchwise manner.

The following example illustrates the present invention.

EXAMPLE I

N,N-dimethylaniline (DMA), hexamethylenetetramine (HMTA), acetic acid (HOAc) and water ($H_2O$) were all charged to a 300 mL stainless steel Magnedrive Autoclave Engineers stirred tank reactor. Toluene was added to the reaction mixture in some instances. The autoclave was then flushed with a nitrogen purge and subsequently heated to temperatures of 135° C. to 160° C. for about 1 to 2 hours. All runs and the particular molar quantities of reactants, based upon 1 mole of DMA are given below. Product yields were determined by gas chromatographic analysis with cyclohexylbenzene as internal standard. The organic phase was analyzed directly, while the aqueous phase was diluted with an equal volume of methanol to ensure injection of a homogeneous sample.

TABLE I

| Run | Mole Ratio of Reagents[a] | | | | Rxn. Temp., °C. | DMA Conv., mol % | Sel. to DMAB, mol % | Yield of DMAB, mol % |
| --- | --- | --- | --- | --- | --- | --- | --- | --- |
| | HMTA | HOAc | H$_2$O | Toluene | | | | |
| 1 | 1 | 1 | 3 | 3 | 135 | 46 | 60 | 28 |
| 2 | 1 | 6.7 | 3 | — | 135 | 66 | 76 | 50 |
| 3 | 1 | 3.3 | 3 | — | 135 | 62 | 69 | 43 |
| 4 | 1 | 1 | 3 | 3 | 135 | 52 | 54 | 28 |
| 5 | 1 | 2 | 3 | 3 | 135 | 56 | 65 | 36 |
| 6 | 0.5 | 1 | 3 | 3 | 135 | 22 | 81 | 18 |
| 7 | 0.5 | 2 | 3 | 3 | 135 | 64 | 84 | 54 |
| 8 | 0.5 | 2 | 3 | 3 | 150 | 75 | 90 | 68 |
| 9[b] | 0.5 | 3 | 3 | 3 | 150 | 72 | 99 | 71 |
| 10[c] | 0.5 | 1 | 3 | 3 | 150 | 31 | 58 | 18 |
| 11 | 0.5 | 1 | 3 | 3 | 150 | 44 | 94 | 41 |
| 12 | 0.5 | 2 | 6 | 3 | 160 | 79 | 75 | 59 |

[a]Relative to 1 mole of DMA
[b]1.25 mol HCOOH added to reaction mixture.
[c]0.3 mol citric acid added to reaction mixture.

This example demonstrates that the reaction of N,N-dimethylaniline with hexamethylenetetramine can be carried out with the addition of toluene to the reaction medium to give dimethylaminobenzaldehyde directly in high yield in one step. There is no need for an additional hydrolysis step since the initially formed Schiff's base is converted to the desired product, p-dimethylaminobenzaldehyde (DMAB) under the reaction conditions. In addition, there is substantial reduction in the amounts of hexamethylenetetramine (0.5 compared to 1.5 mol) and acetic acid (2-3 compared to 7 mol) required to obtain comparable yields of dimethylaminobenzaldehyde when toluene is added compared to its absence. The inventive process gives very high selectivity (>90%) to the desired product, which affords efficient utilization of starting materials.

Reasonable variations and modifications are possible from the foregoing without departing from the scope of this invention.

I claim:

1. A process for the production of N,N-dihydrocarbylaminobenzaldehyde or N,N-dihydrocarbylaminobenzylketone of the formula

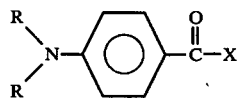

consisting of reacting N,N-dihydrocarbylaniline of the formula

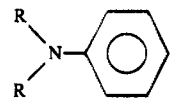

and a protected Schiff's base, derived from the reaction of ammonia and an aldehyde of the formula R'CHO, in the presence of a carboxylic acid of the formula R"COOH, an aromatic hydrocarbon of the formula

and water wherein R is a C$_1$ to C$_8$ hydrocarbyl radical, R' and X are either H or a C$_1$ to C$_{10}$ hydrocarbyl radical, R" is either hydrogen or a C$_1$ to C$_6$ alkyl radical and n is a whole number from 0 to 6.

2. A process as in claim 2 wherein said protected Schiff's base is present in the range of 1-10 moles, said carboxylic acid is present in the range of 0.5-20 moles, said water is present in the range of 1-20 moles and said aromatic hydrocarbon is present in the range of 1-20 moles per mole of said dihydrocarbylaniline.

3. A process according to claim 2 wherein said protected Schiff's base is present in the amount of 0.2-20 moles, said carboxylic acid is present in the amount of 1-10 mole, said water is present in the amount of 2-10 moles, and said aromatic hydrocarbon is present in the amount of 2-10 moles.

4. A process according to claim 2 carried out at a temperature of from about 120° C. to about 175° C. for about 0.5 to about 4 hours.

5. A process according to claim 4 carried out at 150° C. for 1 hour.

6. A process according to claim 3 wherein R is CH$_3$, R' is H and n is 1.

7. A process according to claim 6 wherein R" is CH$_3$.

* * * * *